(12) United States Patent
Korlach

(10) Patent No.: US 7,931,867 B2
(45) Date of Patent: *Apr. 26, 2011

(54) UNIFORM SURFACES FOR HYBRID MATERIAL SUBSTRATES AND METHODS FOR MAKING AND USING SAME

(75) Inventor: Jonas Korlach, Castro Valley, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/981,638

(22) Filed: Oct. 31, 2007

(65) Prior Publication Data

US 2008/0145278 A1  Jun. 19, 2008

Related U.S. Application Data

(63) Continuation of application No. 11/604,543, filed on Nov. 27, 2006.

(60) Provisional application No. 60/740,052, filed on Nov. 28, 2005.

(51) Int. Cl.
*G01N 21/64* (2006.01)

(52) U.S. Cl. ............ 422/82.08; 422/50; 422/82.05; 422/82.09; 422/82.11; 422/98; 422/425; 422/426; 435/4; 435/6; 435/287.2; 435/288.4; 435/288.5; 435/288.7; 204/403.01; 204/403.07; 204/418; 204/643; 205/188; 205/777.5; 205/201.3; 205/208.1; 205/216; 205/225; 205/251; 205/353; 205/492.1; 257/253; 257/414; 257/750; 324/71.1; 359/230; 359/245; 359/318; 359/330; 359/346; 385/12; 385/31; 385/37; 385/116; 385/122; 385/126; 385/129; 385/132; 427/437; 428/215; 430/317; 430/321; 436/164; 436/518; 436/531; 438/1; 438/48; 438/71; 438/116; 438/618; 506/16; 506/18; 600/377; 720/719

(58) Field of Classification Search .......... 422/50, 422/82.05, 82.08, 82.09, 82.11, 98, 425, 422/426, 57; 435/4, 6, 287.2, 288.4, 288.5, 435/288.7; 204/403.01, 403.07, 418, 643; 205/188, 777.5, 201.3, 208.1, 216, 225, 251, 205/353, 492.1; 257/253, 414, 750; 324/71.1; 359/230, 245, 318, 330, 346; 385/12, 31, 385/37, 116, 122, 126, 129, 132; 427/437; 428/215; 430/317, 321; 436/164, 518, 531; 438/1, 48, 71, 116, 118, 618; 506/16, 18; 600/377; 720/719

See application file for complete search history.

(56) References Cited

U.S. PATENT DOCUMENTS

| 2,559,389 A | 7/1951 | Beeber et al. |
| 5,624,711 A | 4/1997 | Sundberg et al. |
| 5,922,537 A * | 7/1999 | Ewart et al. .............. 435/6 |

(Continued)

FOREIGN PATENT DOCUMENTS

WO  WO 2007/041394 A2  12/2007

OTHER PUBLICATIONS

Levene et al, "Zero-Mode Waveguides for Single-Molecule Analysis at High Concentrations", Science, Jan. 31, 2003, vol. 299, pp. 682-686.*

(Continued)

*Primary Examiner* — Lyle A Alexander
*Assistant Examiner* — Dennis M White
(74) *Attorney, Agent, or Firm* — Robert H. Reamey

(57) ABSTRACT

Devices, systems and methods of using same where hybrid substrate materials are provided with a substantially uniform surface to provide uniformity of properties, including interaction with their environments. Uniform surfaces are applied as coatings over, e.g., hybrid metal/silica, metal/polymer, metal/metal surfaces to mask different chemical properties of differing regions of the surface and to afford a protective surface for the hybrid structure.

11 Claims, 5 Drawing Sheets

U.S. PATENT DOCUMENTS

| | | | |
|---|---|---|---|
| 6,255,209 | B1 | 7/2001 | Doan et al. |
| 6,649,403 | B1 * | 11/2003 | McDevitt et al. .......... 435/288.5 |
| 7,056,661 | B2 | 6/2006 | Korlach et al. |
| 7,170,050 | B2 * | 1/2007 | Turner et al. ................. 250/251 |
| 2003/0174992 | A1 * | 9/2003 | Levene et al. ................. 385/129 |
| 2004/0043527 | A1 * | 3/2004 | Bradley et al. .................. 438/48 |
| 2007/0188750 | A1 | 8/2007 | Lundquist et al. |

OTHER PUBLICATIONS

International Search Report and Written Opinion dated Aug. 15, 2007 for related case PCT/US2006/045429.

International Preliminary Report on Patentability dated Jun. 12, 2008 for related case PCT/US2006/045429.

* cited by examiner

Figure 4
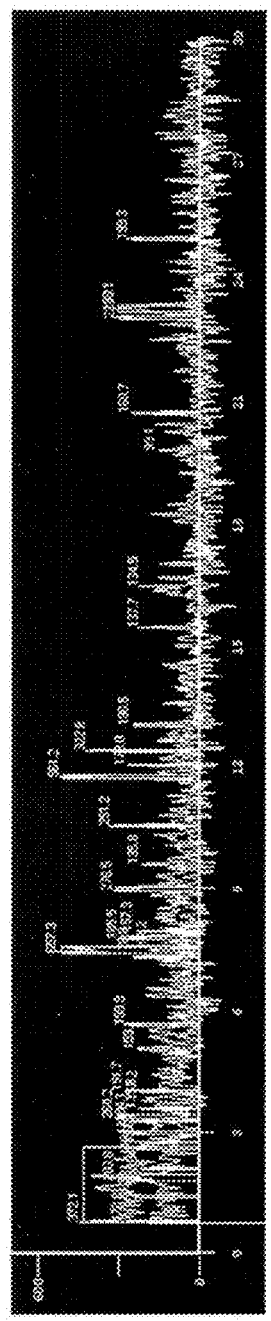
Figure 4A
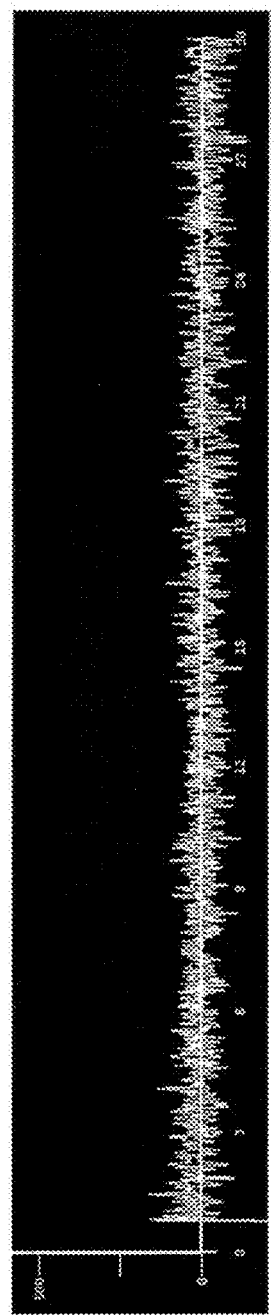
Figure 4B

UNIFORM SURFACES FOR HYBRID MATERIAL SUBSTRATES AND METHODS FOR MAKING AND USING SAME

CROSS-REFERENCE TO RELATED APPLICATIONS

This application is a continuation U.S. patent application Ser. No. 11/604,543 filed Nov. 27, 2006, which claims priority to Provisional U.S. Patent Application No. 60/740,052, filed Nov. 28, 2005, the full disclosure of which is incorporated herein in its entirety for all purposes.

STATEMENT REGARDING FEDERALLY SPONSORED RESEARCH

Not Applicable

BACKGROUND OF THE INVENTION

In a number of analytical operations, the interactions between the material being analyzed and the environment or vessel in which it is being analyzed can have substantial impact on the overall analysis. For example, in the chemical or biochemical analysis of fluid based materials, interactions of analytes or other sample components with the surfaces of the vessel in which the materials are being analyzed, e.g., plastic or glass test tubes, capillaries, etc. can impact the results of the analysis. Such interactions can include adsorption through charge based or hydrophobic/hydrophilic interactions, covalent coupling, repulsive interactions, pH effects, and myriad other effects. A number of strategies have been devised to reduce such effects, including the use of hydrophobic layers, e.g., polytetrafluoroethylene (Teflon®), use of surfactants, and use of surface masking dynamic coatings. The problems of surface interactions with an analytical sample are even more problematic when the surface includes a hybrid surface of different materials where each material region possesses different properties. As a result, it is increasingly difficult to provide a single solution to surface property problems that may be substantially different in character. The present invention provides solutions to these and other related problems.

BRIEF SUMMARY OF THE INVENTION

The present invention is generally directed to hybrid substrate surfaces that further include a uniform masking or coating layer or layers deposited thereon. The substrates of the invention are typically applied in the handling and/or analysis of chemical and/or biochemical materials where it is useful to provide uniform surface properties, but where hybrid substrates are otherwise desirable. Particularly preferred examples include optical arrays for use in biochemical analyses where the arrays of optical elements are fabricated using two or more materials that include different interactive properties with their environments, such as chemical, electrochemical, or physical interactions. In certain embodiments, such materials include transparent and opaque materials having substantially different surface characteristics, e.g., silica based materials and metals.

In at least a first aspect, the invention provides an analytical substrate, comprising a first layer comprising a first surface having at least first and second material regions. The first and second material regions typically include one or more chemical or physical properties that differ when the first and second regions are exposed to a first chemical environment. A second layer is disposed over at least one of the first and second material regions to provide a second surface to the substrate, wherein the second surface that is substantially uniform with respect to the one or more chemical or physical properties, when the second surface is exposed to the first chemical environment.

Relatedly, the invention also provides a layered structure, comprising a first layer substrate comprised of a first material having a first surface. A second layer is also provided disposed upon, but not completely covering the first surface of the first layer, having a second surface, the second layer being comprised of a second material having dissimilar chemical properties from the first layer. A third layer is disposed over the second surface and exposed portions of the first surface, the third layer providing a third surface having substantially uniform chemical properties.

In application, the invention also provides an analytical device, comprising a receptacle for receiving an analytical fluid. A substrate is disposed within the receptacle, where the substrate comprises a first layer comprised of a first material and having a first surface, a second, discontinuous layer disposed upon the first surface of the first layer, the second layer comprised of a second material different from the first material, and a third substantially continuous layer disposed over the second layer to provide a uniform surface exposed to the analytical fluid/protect the first or second layer from the analytical fluid/prevent differential interaction between the analytical fluid and any one of the first, second or third layers.

In another aspect, the invention provides a method of performing an analytical reaction, comprising providing a substrate or analytical device of the invention, and providing a reaction fluid upon the first surface of the substrate or device that comprises the first chemical environment, and performing the analytical reaction in the reaction fluid.

The invention also provides a method of producing an analytical substrate, comprising providing a first transparent layer having a first surface. A second discontinuous layer is provided over the first surface of the first transparent layer, resulting in a second surface comprised of exposed portions of the first surface of the first transparent layer and the second discontinuous layer. A third layer is deposited over at least one of the discontinuous layer and the exposed portions of the first surface of the transparent substrate, to provide a third surface that is substantially uniform with respect to the one or more chemical or physical properties, when the third surface is exposed to the first chemical environment.

The invention also provides a system, comprising a substrate of the invention in conjunction with an optical detection system positioned to receive optical signals from a reaction fluid disposed upon the substrate.

BRIEF DESCRIPTION OF THE DRAWINGS

FIG. 4A is a plot of background fluorescent signal over time from a control surface and FIG. 4B is a coated surface exposed to a fluorescent reagent.

DETAILED DESCRIPTION OF THE INVENTION

Figure 1:
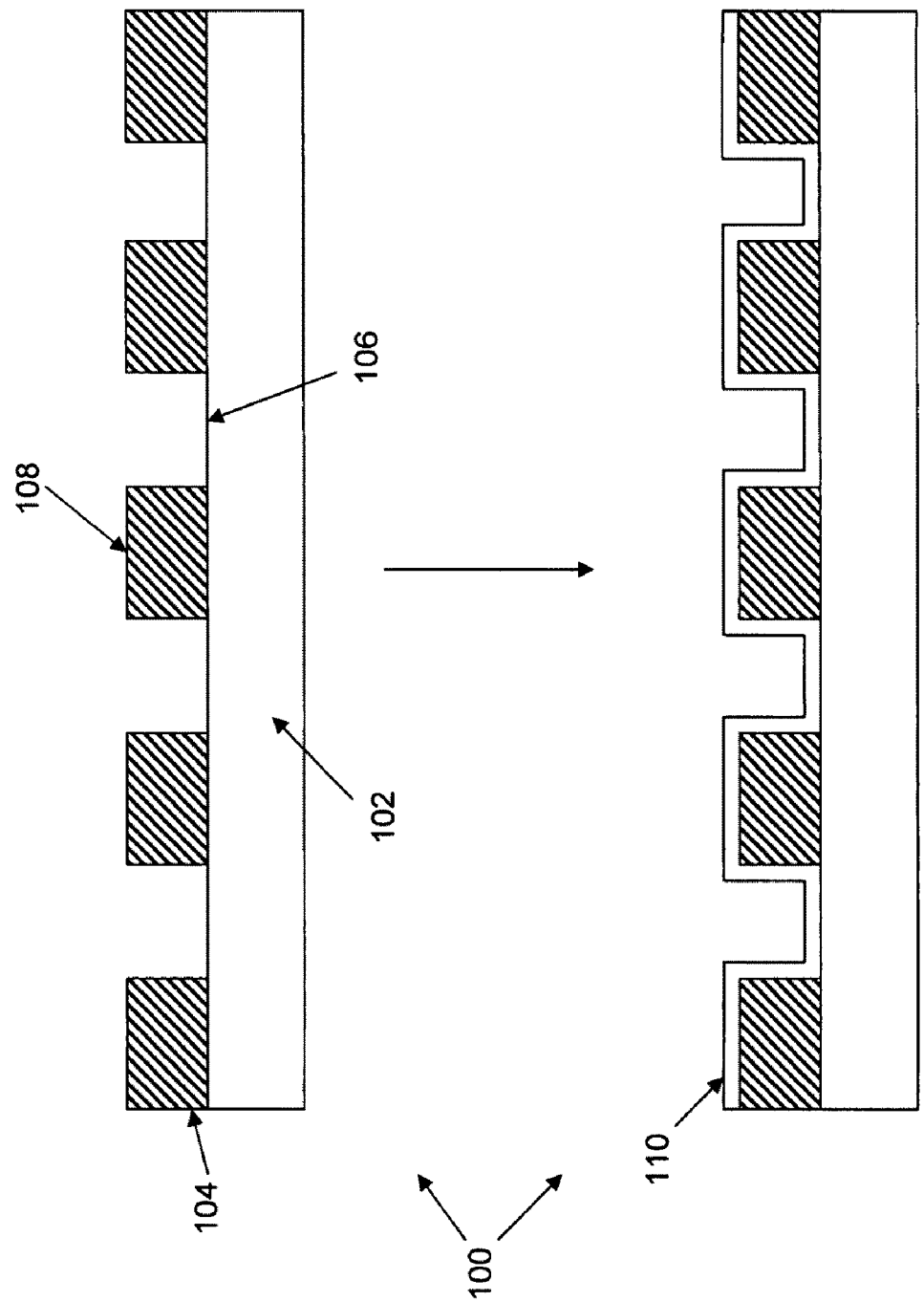
FIG. 1 is a schematic illustration of a hybrid substrate surface of the invention that is processed to include a uniform layer deposited over it.

The present invention is generally directed to mixed material substrates, and particularly those used in analytical operations for chemical, biochemical and biological analyses. Mixed material substrates may be broadly employed in a variety of analytical operations. For example, such substrates may include transparent and opaque materials to provide optical windows or confinements, may include conductive and insulating materials to carry electrical current for the operation or analysis of analytical devices, or they may include structural components that are derived from different materials that are employed due to other benefits, e.g., easier manufacturing. The invention is also directed to methods and processes for producing the substrates of the invention, and the use of such substrates in chemical and/or biochemical analyses.

By way of example, in certain particularly preferred aspects, such substrates comprise a first transparent layer over which is deposited a discontinuous layer that provides one or more functional attributes to the substrate in a desired operation, such as generation of electromagnetic fields, provision of optical windows or confinements, definition of structural features, e.g., micro or nano-wells, or the like. In some cases, the discontinuous layer will comprise an opaque material that can have dramatically different chemical and/or physical properties from the underlying substrate layer, resulting in a surface that may interact with its environment in dramatically different ways.

In an exemplary application, an array of optical confinements may be provided as a layer of opaque material disposed upon a transparent substrate layer, where the optical confinements are defined as apertures through the opaque layer. The resulting substrate thus possesses an overall surface that has at least two different material properties, namely that of the opaque layer and that of the underlying, but at least partially exposed substrate layer. Because these two material layers are selected to perform differing functions, e.g., transparency vs. opaqueness, it is not surprising that their material properties in the given analysis, e.g., their interaction with the components of the analysis, would differ. As will be appreciated, such differences in the performance of a given analysis can have far reaching effects on the analysis. For example, such differential interaction may result in localization of reagents to one material or the other, it may result in creation of locally differing chemical or electrical environments, or it may result in adverse interactions between the fluid reactants and one or both of the layer components, e.g., oxidation, corrosion, or the like.

As noted above, despite the benefits of such mixed material surfaces, there are also potential drawbacks to such surfaces, particularly where the physical and/or chemical properties are substantially different, e.g., electrochemically. Accordingly, and as alluded to above, at least a first aim of the invention is to provide mixed material substrates that provide a uniform surface exposed to the analytical reactants that are used in the application to which the substrate will be put. In particular, by providing a uniform surface exposed to such reactants, one avoids any differential interaction between one or more of the reactants, or other constituents of the application and one of the materials in the substrate. As a result, the reaction conditions may be optimized to avoid any adverse interactions between such reactants and the substrate, as a whole. Such adverse interactions include associative interactions resulting from surface charges and/or hydrophobic/hydrophilic interactions, chemical reactions at the surface, e.g., oxidation/reduction reactions. In addition to shielding reactants from adverse consequences associated with surface interaction, the invention also provides a measure of protection for the surface from adverse interactions with any components of the reaction mixtures. Such interactions include, e.g., corrosive interactions with reagents having high ionic strength, or low or high pH, oxidation of the substrate components, or the like, that might detract from the operation and/or application of the substrate for its desired use.

In accordance with the present invention, a base substrate or first layer is provided. The first substrate layer typically comprises a solid material that may be rigid or flexible, and may be transparent or opaque. In particularly preferred aspects, the first substrate layer comprises a rigid or flexible transparent substrate layer, in order to provide optical access to a reaction vessel or receptacle for which the substrate provides a wall or floor. A variety of substrate materials may be used that fit these requirements, such as inorganic substrates, like silica based substrates such as glass, quartz, fused silica, or the like. In terms of flexible substrates, thin inorganic layers and/or flexible polymeric materials may be employed, such as polymethylmethacrylate (PMMA), polypropylene, polystyrene, polyethylene, PDMS, or any of a variety of other flexible and preferably substantially transparent substrate materials.

Also as alluded to above, the devices of the invention may also include a second, discontinuous layer disposed on the first layer such that it provides portions of the overall surface that are comprised of a different material than the exposed portions of the underlying first layer. While a second discontinuous layer is generally the structure that imparts the mixed material substrates of the invention, it will be appreciated that the mixed material substrate also encompasses two different materials that are integrated into a single substrate. By way of example, a mixed material substrate of the invention would include substrates where a given layer includes regions of a first material and regions of a second material that possesses such different physical or chemical properties. For example, where a single substrate layer is fabricated from different polymer materials in different regions such that the different regions possess different properties, or for silica based substrates that have been subjected to localized ion implantation, e.g., to provide regions of different conductivity or having different optical characteristics, or that have different regions that have been oxidized or otherwise chemically or physically altered to yield such different properties.

With respect to layered substrates, a schematic illustration of the substrates of the invention is provided in FIG. 1. As shown in the upper panel, the overall substrate 100 includes a base substrate layer 102. As noted herein, such base substrate may include any of a variety of different materials, including transparent materials, such as glass, fused silica, quartz or a polymeric material. A second, discontinuous layer 104 is provided on the surface of base substrate layer 102. The discontinuous layer 104 is typically comprised of a material that is different from the underlying substrate layer 102. By way of example, and as noted elsewhere herein, for certain optical applications, the discontinuous layer 104 typically includes an opaque or non-transparent material, including, e.g., a metal layer, a semiconductor layer, or the like. The discontinuous layer 104 includes openings to the underlying surface 106 of the underlying base substrate layer 102. As a result of the exposure of portions of surface 106 the underlying substrate layer 102, and the surface 108 of the discontinuous layer 104, the overall surface of the substrate 100 includes regions that are comprised of different materials, and as a result, include different properties. In accordance with the invention, and as shown in the lower panel, a coating layer 110 is provided over the discontinuous surface to provide a substantially uniform surface on the overall substrate 100.

Figure 2:
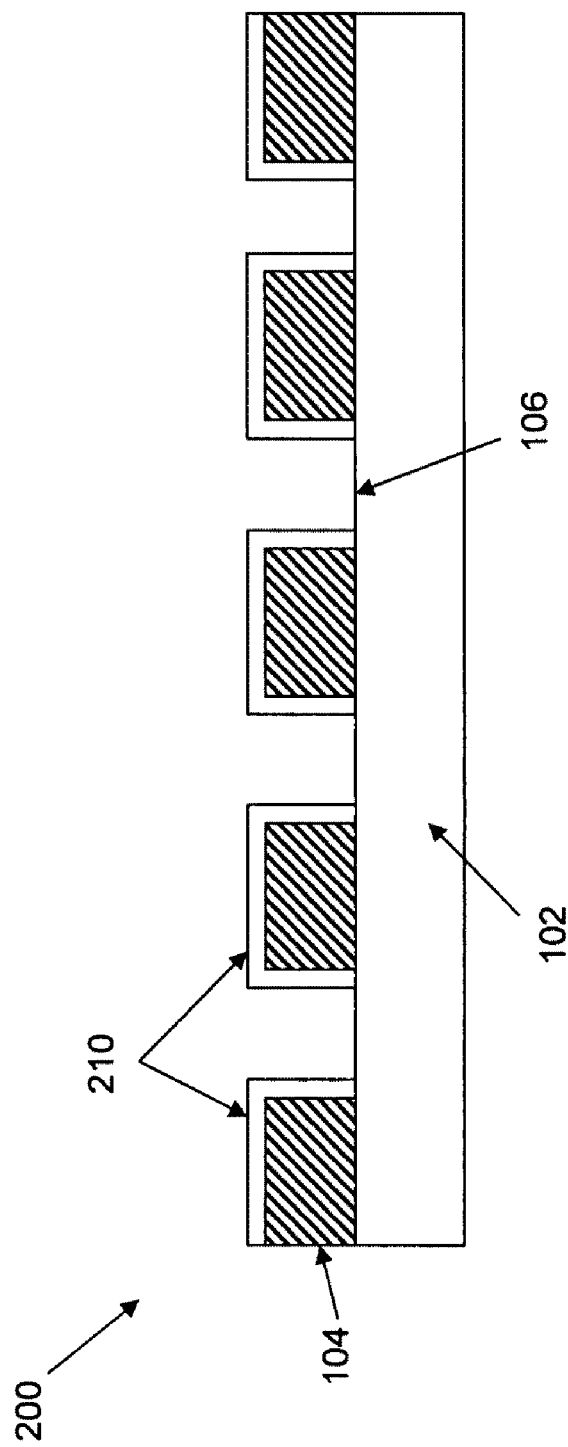
FIG. 2 is a schematic illustration of a hybrid substrate surface of the invention having a uniform surface as a result of having a coating layer deposited over one of two different material making up the hybrid surface, to yield a uniform surface.

In alternative aspects, and as shown in FIG. 2, the coating layer 210 may be provided only over the surface of one of the materials that make up the overall surface of the substrate 200, e.g., the discontinuous layer 104, by utilizing a coating material that associates preferentially with that material. This aspect may be useful where the coating layer results in a surface that is substantially similar to the underlying substrate layer 102 or its surface 106, thus yielding a substantially uniform surface over the entire substrate 200. In general, one could utilize the differential properties of the two different materials to tune the association of the coating material to the discontinuous layer. In particular, in the case of metal/glass hybrid surfaces, the glass surface will typically comprise a negative charge, while a metal oxide surface, e.g., aluminum oxide, may be positively charged. By coating with a negatively charged coating material, e.g. a negatively charged silane, polymer, or the like, one may gain selective coating of only the metal surfaces.

As will be appreciated by the skilled artisan, substrates conforming to this general configuration have a variety of applications. For example, layered substrates may be employed to provide structural components upon an otherwise planar surface, e.g., to provide posts, wells, channels, troughs, trenches, or the like, for exploitation in the localization, direction, and/or observation of materials over the surface of the device.

Likewise, such layered structures may be used to provide layers of differing functionality, e.g., providing electrically conductive components over the surface of an otherwise insulating substrate to provide electrical access to one or more regions of the surface of the overall device, e.g., to drive electrophoretic movement of materials, sense reactions, e.g., in potentiometric or field effect sensors, etc.

Such substrates may additionally be used to provide optical features upon an otherwise uniform substrate material. Examples of such optical features include simple components, such as merely providing an isolated window for observation of a reaction fluid within a selected region of the surface of the overall substrate. Alternatively or additionally, such optical components may provide for optical manipulation of incident or emitted light from or through the substrate, e.g., as an optical grating or optical confinement, i.e., a waveguide, a zero mode waveguide, as a mask for performing selective optical analyses, or for performing differential optical analysis, e.g., using optical filtering regions, or the like.

The various applications of mixed material substrates, as described above, envisions a broad range of different materials that range from transparent materials to opaque, from organic to inorganic, from conductive to semiconductive to insulative, and to a variety of different structures, including layered structures, discontinuously layered structures, embedded structures or materials, and the like. While the present invention is applicable to this full range of applications, materials, and structures, for ease of discussion, the present invention is generally illustrated in terms of the most preferred application of a discontinuous opaque, and preferably metal, layer disposed upon a planar transparent substrate layer that is preferably a rigid material. Particularly preferred examples of such substrates include transparent silica based substrates, such as glass, quartz, fused silica, or the like, having a discontinuous metal layer disposed upon its surface where the discontinuities in the metal layer provide apertures through the metal layer for observation of events upon or adjacent to the exposed surface of the underlying transparent substrate layer. Particularly preferred embodiments of such substrates include, for example, waveguide structures and zero mode waveguide structures, where a metal layer is deposited upon a transparent substrate as a cladding for the waveguide, and apertures are disposed through the metal layer to provide the core of the waveguide. Zero mode waveguides are described in, for example, U.S. Pat. No. 6,917,726, which is incorporated herein by reference in its entirety for all purposes.

Briefly, such zero mode waveguides typically comprise a metal cladding layer, e.g., aluminum, deposited upon an underlying transparent substrate layer, e.g., glass, quartz or fused silica. Small apertures are disposed through the cladding layer to the underlying substrate, and form a core region for the waveguides. As an aperture through the cladding layer, in application in chemical or biochemical analyses, the core is typically filled with the analytical reaction fluid. The cross sectional dimension of the core is typically sufficiently small as to prevent light of a frequency that is greater than a cut-off frequency from propagating completely through the zero mode waveguide. For typical chemical and biochemical analyses that rely upon light direction and detection for light of wavelengths 400 nm to about 900 nm, this cross sectional dimension will typically be from about 10 nm to about 200 nm, and in some cases between about 20 nm and about 100 nm. As a result light directed at one end of the core, e.g., through the transparent substrate layer, will only penetrate the core a short distance.

The result is the effective illumination of a very small volume of the core region at the base of the waveguide. This small volume illumination is particularly useful for analysis of single molecule or few molecule reactions (e.g., as described in published U.S. Pat. Nos. 7,033,764, 7,052,847, 7,056,661, 7,056,676, the full disclosures of which are incorporated herein by reference in their entirety for all purposes).

Other exemplary substrates along this line include those that utilize an opaque aperture to provide limited access to or from an observation region, so as to restrict what is being observed, either by limiting illumination or emission from such region.

A variety of other devices fit the general profile of the substrates that are improved by the present invention, including micro electromechanical systems (MEMS), in which metal or other different material layers are used to provide conductive paths to different regions of the substrate surface, or otherwise to provide a varied functionality of the surface.

The presence of a discontinuous metal layer disposed upon a different material provides the potential of differential interactions of the various surface components with the surrounding environment, and particularly in the case of fluidic, reactive environments. By way of example, the nature of a metal surface in a high ionic strength aqueous environment is substantially different from that of a silica based, e.g., glass surface. Initially, such surfaces will potentially have substantially different interactions with reactants within the aqueous system based upon differing charges and relative hydrophobicity. In the case of biochemical reactions, such differential reactions can impact critical reagents, such as substrates and products, proteins, enzymes, cofactors, labeled materials, cells, salts, and the like. One of the most problematic differential interactions results from the preferential localization (or repulsion) of one or more reactants to a particular component of the surface. Preferential localization of a particular reagent or product can result in aberrant results stemming from locally high or low concentrations of the given reagent, excessive signal noise resulting from optically active components localizing in one or more locations, and the like.

In addition to adverse impacts on reactants within an observed reaction system, interactions between reaction components and a portion of the surface of the device can also have adverse impacts upon one or both substrate layers. For example, in the case of metallic layers in contact with aqueous systems, and particularly high ionic strength aqueous solutions, such layers may be subject to degradation, corrosion or other conversion that adversely impacts their operation.

The present invention generally provides the above-described mixed material substrates with a uniform coating of an additional layer of material that provides a substantially uniform and preferably substantially continuous layer over the hybrid surface of the first and second layers. Provision of such a uniform surface over a hybrid surface provides an opportunity to select a coating material that is most compatible with the ultimate application environment of the surface. For example, in terms of chemical or biochemical analyses, such surfaces are generally exposed to aqueous reaction mixtures that may range in salt concentrations from salt free to multimolar salt concentrations, and may range from highly acidic to highly basic, e.g., from pH 2.0 to 9.0. For purposes of the invention, such environments are referred to as chemical environments.

Alternatively or additionally, provision of a uniform, and preferably substantially continuous, surface layer over a hybrid material surface provides a single material surface against which the environmental conditions may be optimized for minimal adverse interactions. Such environmental conditions might include an ultimate application, e.g., exposure to reagents, buffers, and the like, in an analytical application, or it may include a subsequent treatment step, e.g., further surface modification, whereby one has converted a hybrid surface to a uniform surface for further manipulation.

As noted above, in some aspects, the additional coating layer may be selectively applied to one material region and not the other, so as to yield a resulting surface that has uniform properties, at least with respect to some, if not all chemical and/or physical properties, e.g., including the particularly relevant chemical or physical properties of interest. Thus, as used herein, uniformity of a surface may apply to one or more chemical and/or physical properties of the surface, and with respect to chemical analyses will typically include such properties as chemical composition of the surface, surface charge or zeta potential of the surface, relative hydrophobicity or hydrophilicity of the surface, oxidative or reductive potential of the surface, surface roughness, availability and density of reactive moieties on the surface, including the reactivity of such groups toward derivatizing chemicals, and the like. For example, where surface charge is the most critical component, a coating layer that provides for uniform surface charge for the overall mixed material surface would be termed uniform.

In addition to providing benefits for interaction with reagents, provision of a uniform and preferably substantially continuous coating layer over a hybrid material surface can provide protection for the underlying surface components from adverse impacts of reagents or reactive environments with the underlying surface components, e.g., that might cause corrosion or conversion of one or more of the surface components. Such adverse impacts are accentuated in hybrid material systems that may not be selected for compatibility with each of the different materials on the substrate.

A variety of different coating materials may be applied to the hybrid surfaces of the invention, including organic coatings such as polymers, e.g., PEGs, fluorinated polymers, i.e., polytetrafluoroethylene (Teflon®), organosilicates, i.e., methylsilsesquioxanes (MSQ), organosilanes, i.e., PDMS, and inorganic coatings, i.e., silicon oxides ($SiO_x$), e.g., $SiO_2$, spin-on glass (SOG), and the like. As noted above, a number of different materials comprise silica based materials, e.g., glass, quartz, silicon, PDMS, and the like.

The method used to apply the coating layer will typically depend, to some extent upon the material that is to be coated. In general, however, liquid phase or vapor phase coating techniques are generally used in accordance with the present invention, as are sputtering methods for applying coating materials. Liquid phase methods include spin coating methods, immersion methods, self assembly (e.g., of monolayer, bilayer, or other film coatings) processes. Such methods may include additional curing or conversion steps to finish the coating layer, e.g., a thermal curing or annealing step, in the case of spin-on glass and silicate polymers.

Vapor deposition methods include chemical vapor deposition (CVD) methods, including plasma enhanced methods (PECVD), molecular vapor deposition (MVD), atomic layer deposition (ALD). Sputtering methods for provision of uniform layers are also useful in the context of the invention, e.g., sputtering uniform silicon oxide layers over a mixed material substrate. These and a variety of other coating methods are generally known in the art of semiconductor fabrication and processing.

As noted previously, a particularly preferred application of the present invention is to optical confinement structures, like zero mode waveguides, and arrays of such structures. Zero mode waveguides generally comprise a cladding layer that surrounds a core region through which electromagenetic energy is propagated. In preferred aspects, the core comprises an opening disposed through the cladding layer, e.g., the core material is air or other present fluid. The dimensions of the waveguide are typically selected so that electromagnetic energy that enters the core is propagated only partially through the core. See, e.g., Levene et al., Science (2003) 299:682-686.

In preferred contexts, waveguides or waveguide arrays are defined by a metal cladding layer disposed over a transparent substrate, e.g., glass, quartz, fused silica, or transparent polymer, such that the resulting surface comprises both metal and the transparent substrate. In the case of fused silica, it will be readily appreciated that the surface properties of the metal cladding, e.g., aluminum, chromium, or the like, are very different from the highly charged fused silica surfaces. Typically, such metal layers are deposited upon underlying substrates utilizing well known IC processing techniques, such as thermal evaporation, sputtering, and the like. As noted above, other methods may be employed to generate differential material surfaces where metals are not employed, including ion implantation, embedding of polymer layers via lamination etc.

Where the above-described arrays are to be applied in chemical and biochemical analyses, the differential surface properties can have an even greater impact in interacting differently with components of analyses, e.g., reagents such as enzymes, substrates or products, buffers, salts, or the like.

Accordingly, when applying these waveguide structures to chemical or biochemical analyses, it is generally desirable to provide a uniform and preferably substantially continuous layer over the metal layer and the exposed regions of the underlying substrate. As stated herein, this provides a single surface against which subsequent surface environments may be optimized, including, for example treatments for immobilizing reaction components within the waveguide cores, treatments for passivating the surface against excessive adsorption of reagents that might interfere with the desired analysis, e.g., fluorescent molecules that might provide excessive background signal, or the like. Examples of waveguide structures including such surface treatments are described, for example, in U.S. patent application Ser. No. 11/240,662, filed Sep. 30, 2005, and incorporated herein by reference in its entirety for all purposes. Such methods typically employ diluted surface functionalities, e.g., diluted during or after their adsorption or coupling to the surface.

By way of example of the application of the invention to methods of performing analytical reactions, U.S. Pat. No. 7,033,764 (which is incorporated herein by reference in its entirety for all purposes) describes elegant single molecule DNA sequencing processes and systems that would benefit from the methods and devices described herein. Briefly, arrays of zero mode waveguides, e.g., configured in accordance with the present invention, may be employed as optical confinements for single molecule DNA sequence determination. In particular, as noted above, these ZMWs provide extremely small observation volumes at or near the transparent substrate surface, also termed the "base" of the ZMW. A nucleic acid synthesis complex, e.g., template sequence, polymerase, and primer, that is immobilized at the base of the ZMW may then be specifically observed during synthesis to monitor incorporation of nucleotides in a template dependent fashion, and thus provide the identity and sequences of nucleotides in the template strand. This identification is typically accomplished by providing detectable label groups, such as fluorescent labeling molecules, on the incorporating nucleotides. In some instances, the labeled nucleotides terminate primer extension, allowing a "one base at a time" interrogation of the complex. If, upon exposure to a given labeled base, a base is incorporated, its representative fluorescent signal may be detected at the base of the ZMW. If no signal is detected, then the base was not incorporated and the complex is interrogated with each of the other bases, in turn. When a base is incorporated, the labeling group is then removed, e.g., through a photocleavable linking group, and where the label was not the terminating group, a terminator, upon the 3' end of the incorporated nucleotide, may be removed prior to subsequent interrogation.

In alternate and preferred arrangements, the nucleotide analogs are labeled upon one or more of the beta, gamma or other terminal phosphate groups (in the case of tetra or pentaphosphate nucleotide analogs; see, e.g., U.S. Pat. No. 7,041,812, which is incorporated herein by reference in its entirety for all purposes). As a result, the process of incorporation cleaves the labeling group automatically, allowing real-time advancement of the synthesis reaction. Further, because the incorporation event results in prolonged retention of the incorporated nucleotide (and its associated label) within the observation volume of the ZMW, that event can be readily detected. As will be appreciated, the use of single molecule detection methods further enhances the desirability of providing controlled surface interactions with the reaction environment.

In the context of the use with zero mode waveguides, as well as other applications, the application of a uniform coating may be carried out to provide a coating having a desired thickness, in accordance with known processes. In particular, and merely by way of example, a layer may be desired that is substantially uniform and continuous, e.g., impermeable to water, while at the same time not being too thick so as to place reaction volumes outside of the observation region of a waveguide core. In other cases, a selected thickness may be desired to provide reactants at an optimal position relative to the base of the core, the metal cladding or other structural or optical elements of the system. As noted, controlling thickness of layers deposited using the methods described herein, may be accomplished by a variety of known methods, including time controlled vapor deposition processes, concentration controlled fluid based methods, and/or controlled sputtering processes, and the like.

In accordance with the foregoing or any aspect of the invention, it will be appreciated that multiple coating steps may be employed to achieve the desired coating. In particularly preferred aspects, e.g., in the case of PDMS coatings, multiple coatings followed by immersion in water or other aqueous solutions has been shown to reduce non-specific adsorption of dyes to surfaces. As such, the uniform coatings of the invention may be derived from multiple disparate steps, e.g., a coating step followed by an oxidation step or other coating step, in order to achieve desired surface properties.

As will be appreciated, the substrates of the invention are also typically included within kits for carrying out desired applications, that include appropriate reagents for the reaction, that may be provided in pre-measured, volumes and or concentrations for ease of use, along with instructions for carrying out the reactions of interest. For example, in the case of sequencing reactions, such kits, in addition to including the substrates described herein, will typically include one or more of four different nucleotides or nucleotide analogs, e.g., bearing fluorescent labels, nucleic acid polymerase enzymes, in some cases primer sequences, and additional adjunct reagents, e.g., buffers, salts, and the like.

Figure 5:
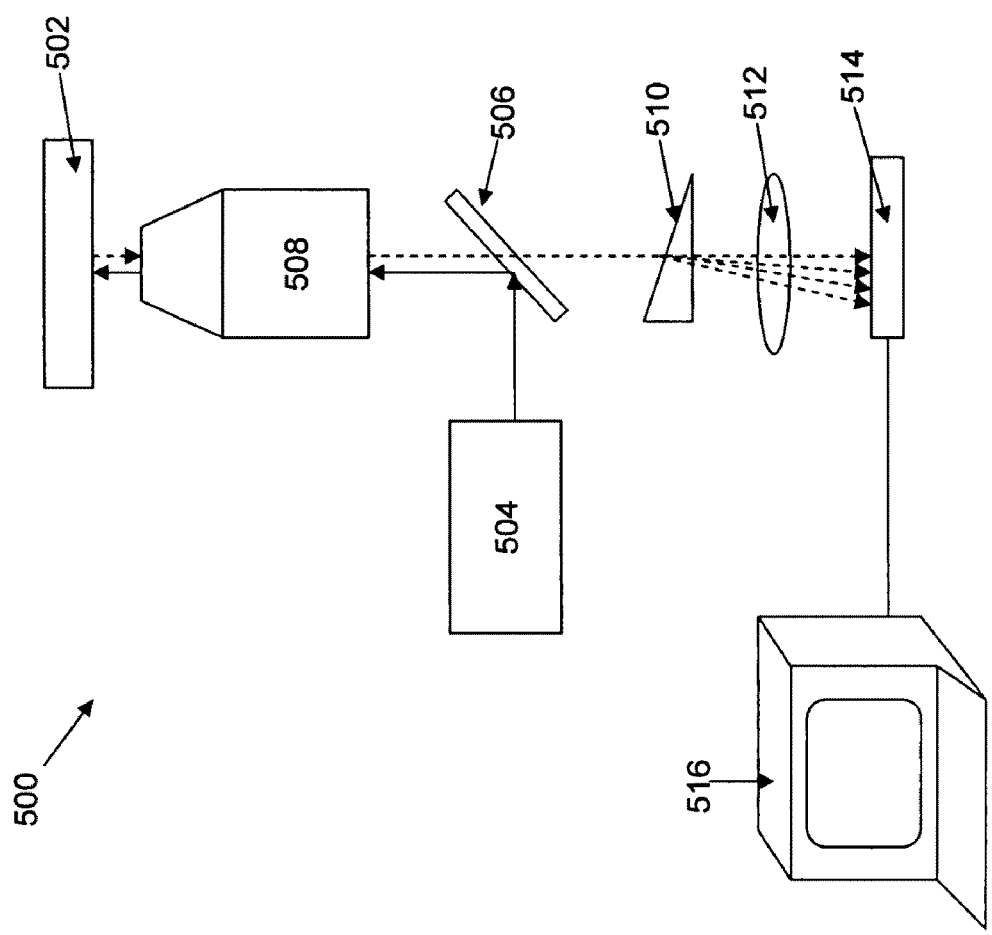
FIG. 5 provides a schematic illustration of a system incorporating a substrate of the invention.

The substrates of the invention will also typically be used in conjunction with overall systems for monitoring and evaluation of the reactions carried out upon the substrates. An example of such a system is illustrated in FIG. 5. As shown, the system 500 will typically include a substrate of the invention 502. In the case of fluorescence based detection of reactions, the system will typically include a light source such as laser 504, that is positioned to direct light of an appropriate wavelength through an optical train that may include a variety of optical elements such as dichroic 506, and objective lens 508, where the optical train is positioned to the light at the substrate 502. Additional optical elements may be included within the optical train, including for example, beam splitters to provide multiple excitation beams directed at the substrate for multiplex applications, beam linearizers, for simultaneous illumination of larger areas of substrates. Fluorescent signals emitted from the substrate or the reactions being carried out thereon, then pass back through optical train and optionally through additional fluorescent signal processing components, e.g., prism 510, focusing lens 512, until they impinge upon a detector, such as charge coupled device (CCD) or electron multiplying CCD (EMCCD) 514. A variety of different types of detectors may be employed in the context of the invention, including photomultiplier tubes (PMTs), photodiodes, avalanche photodiodes, and the like. In preferred aspects, however, imaging detectors are preferred, such as diode array detectors, CCDs, ICCDs, EMCCDs and the like.

The signals detected by EMCCD 514 are then passed to a processor, such as computer 516 where they may be subjected to signal and data processing to yield a user interpretable manifestation of the data, e.g., in a data plot, sequence readout, or the like. Optical systems for use in the invention have been generally described in co-pending PCT Application No. US 2006/38243, and U.S. application Ser. No. 11/483,413, filed Jul. 5, 2006, the full disclosures of each of these is incorporated herein by reference in its entirety for all purposes.

EXAMPLES

Example 1

Vapor Deposited PDMS on Hybrid Zero Mode Waveguide Array Substrates

A zero mode waveguide array that included an aluminum cladding layer surrounding waveguide cores of approximately 50 nm, was subjected to a plasma-based PDMS deposition process.

The waveguide arrays (aluminum cladding on fused silica substrate) were prepared with an acetone wash, isopropanol rinse and nitrogen drying. The arrays were then placed onto a chip holder or a glass slide and plasma treated with the cladding layer up, for 5 minutes (Harrick, Inc., Medium power level setting, 1900-2000 mTorr). The waveguide arrays were then attached to the slide using a UV curable adhesive (Norland 81) so that the array pane of the waveguide was opened to a hole in the slide, which created a well around the array suitable for fluid application.

A polydimethylsiloxane (PDMS) gasket, precut to fit the slide, was then placed onto the slide. The mounted chip was then plasma treated for 1 minute (Low power level setting, 1900-2000 mTorr). Water was deposited in the slide well receptacle, and the device was allowed to incubate at room temperature for between about 0.5 and 2 minutes. The water was removed and the device allowed to dry. The resulting devices were then assayed to determine the level of background signal resulting from non-specific association of fluorescent nucleotide analogs. The steps of plasma treatment, water incubation were then repeated up to 5 times.

Figure 3:
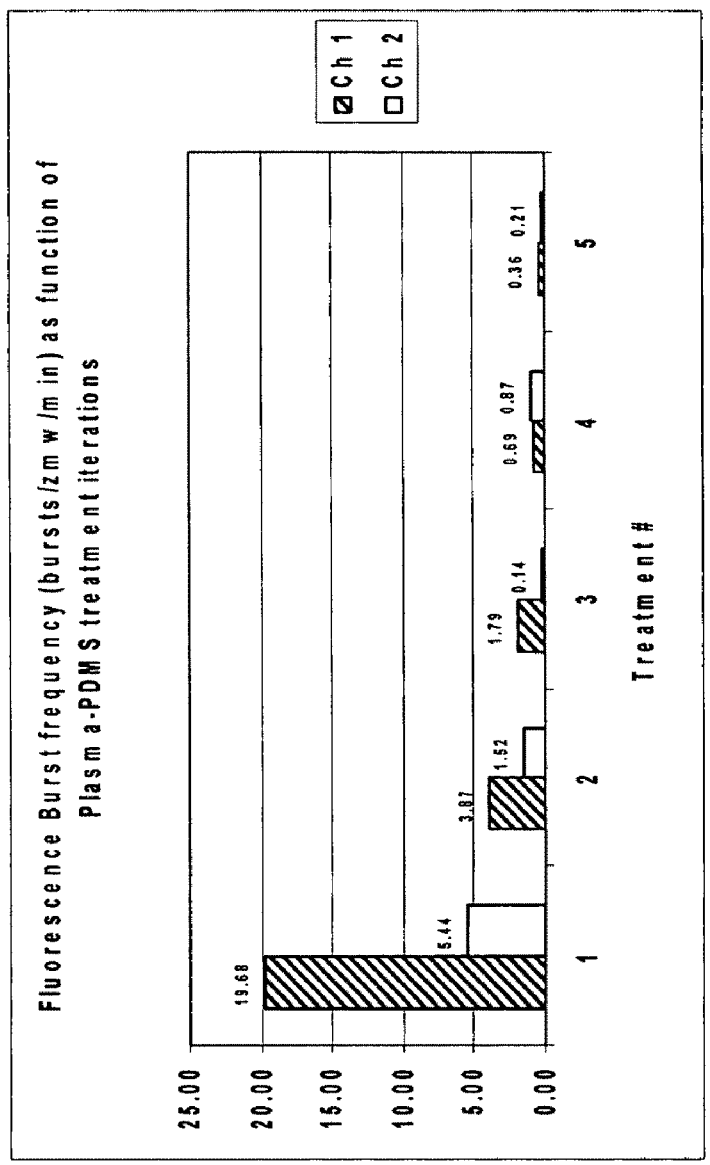
FIG. 3 is a plot of non-specific signal emanating from a substrate surface following successive PDMS coating processes.

FIG. 3 shows a plot of fluorescent burst frequency (fluorescent pulses) resulting from non-specific interaction of two different fluorescent reagents (Alexa546- and Alexa488-labeled nucleoside tetraphosphate analogs, channel 1 and 2, respectively) within the observation region of zero mode waveguides. As can be seen, multiple cycles of plasma assisted deposition of PDMS, or its silane derivatives, yields a substantial quieting of the surface to background noise.

Similarly, a comparison of time-plots, as shown in FIG. 4, of non-specific fluorescent signal intensities in a single cycle PDMS deposition (upper panel) process versus a multiple cycle process (lower panel, 5 cycles of Plasma/PDMS Deposition) shows a decided decrease in background fluorescent noise.

Although described in some detail for purposes of illustration, it will be readily appreciated that a number of variations known or appreciated by those of skill in the art may be practiced within the scope of present invention. Unless otherwise clear from the context or expressly stated, any concentration values provided herein are generally given in terms of admixture values or percentages without regard to any conversion that occurs upon or following addition of the particular component of the mixture. To the extent not already expressly incorporated herein, all published references and patent documents referred to in this disclosure are incorporated herein by reference in their entirety for all purposes.

The invention claimed is:

1. A system, comprising:
a substrate, comprising:
a first layer comprising a first surface having at least first and second material regions, the first and second material regions having one or more chemical or physical properties that differ when the first and second regions are exposed to a first chemical environment, wherein said first material region comprises a transparent material, and said second material comprises an opaque metal with any associated metal oxide; wherein the first layer comprises a layer of the first material and a layer of the second material, wherein the layer of second material is a discontinuous layer disposed over the layer of first material layer resulting in a first surface of the first layer having apertures with exposed regions of first material, the apertures having a cross-sectional dimension that is from about 10 nm to about 200 nm;
a second layer, comprising a coating material that associates preferentially with the second material regions, disposed selectively over second material regions to provide a second surface to the substrate, whereby the coating material covers substantially all of the second material regions, whereby at least portions of the first material regions exposed by the aperture are not coated by the second layer, and wherein the second surface that is substantially uniform with respect to the one or more chemical or physical properties, when the second surface is exposed to the first chemical environment; and
an optical detection system positioned to receive optical signals from a reaction fluid disposed upon the substrate.

2. The system of claim 1, wherein the optical detection system comprises an excitation light source positioned to direct excitation light at the reaction fluid, and a fluorescence detector for detecting fluorescent signals from the reaction fluid.

3. The system of claim 1, wherein the one or more physical or chemical properties are selected from chemical composition, surface charge, relative hydrophobicity, conductivity, oxidative capacity, surface roughness, and density of reactive chemical moieties.

4. The system of claim 1, wherein the first material comprises a silica based material.

5. The system of claim 4, wherein the first material is selected from glass, quartz, and fused silica.

6. The system of claim 1, wherein the apertures have a cross-sectional dimension that is from about 20 nm to about 100 nm.

7. The system of claim 1, wherein the second layer comprises an inorganic layer.

8. The system of claim 7, wherein the inorganic layer comprises a silica based layer.

9. The system of claim 8, wherein the silica based layer comprises silicon oxide.

10. The system of claim 1, wherein the second layer comprises an organic layer.

11. The system of claim 10, wherein the organic layer comprises organic materials selected from organic polymers, organosilicates, and organosilanes.

* * * * *